(12) United States Patent
Sosalla et al.

(10) Patent No.: US 7,520,873 B2
(45) Date of Patent: Apr. 21, 2009

(54) DISPOSABLE ABSORBENT ARTICLE HAVING A COLOR GRADATION FEATURE

(75) Inventors: Paula Mary Sosalla, Appleton, WI (US); Shirlee Ann Weber, Neenah, WI (US); Jennifer L. S. Misek, Little Chute, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 122 days.

(21) Appl. No.: 09/977,062

(22) Filed: Oct. 12, 2001

(65) Prior Publication Data

US 2003/0073966 A1 Apr. 17, 2003

(51) Int. Cl.
*A61F 13/15* (2006.01)
*A61F 13/20* (2006.01)

(52) U.S. Cl. .................................. 604/385.01; 604/364

(58) Field of Classification Search ................. 604/361, 604/364, 385.01; 6/206; 252/408; 128/886
See application file for complete search history.

(56) References Cited

U.S. PATENT DOCUMENTS

| | | | |
|---|---|---|---|
| 4,022,211 A | 5/1977 | Timmons et al. | |
| 4,292,916 A | 10/1981 | Bradley et al. | |
| 4,328,181 A * | 5/1982 | Anders et al. ................. | 422/56 |
| 4,704,116 A | 11/1987 | Enloe | |
| 4,812,053 A | 3/1989 | Bhattacharjee | |
| 4,903,254 A | 2/1990 | Haas | |
| 4,931,051 A * | 6/1990 | Castello ....................... | 604/361 |
| D310,880 S | 9/1990 | Majewski | |
| 4,987,849 A | 1/1991 | Sherman | |
| 5,045,283 A | 9/1991 | Patel | |
| 5,053,339 A | 10/1991 | Patel | |
| 5,058,088 A | 10/1991 | Haas et al. | |
| D325,256 S | 4/1992 | Landsman et al. | |
| 5,597,642 A | 1/1997 | Schleinz et al. | |
| D379,226 S | 5/1997 | Kaczmarzyk et al. | |
| 5,766,212 A * | 6/1998 | Jitoe et al. ................... | 604/361 |
| 6,075,178 A * | 6/2000 | La Wilhelm et al. ......... | 604/361 |
| 6,297,424 B1 * | 10/2001 | Olson et al. .................. | 604/361 |

FOREIGN PATENT DOCUMENTS

| | | |
|---|---|---|
| EP | 0951889 A1 | 10/1999 |
| WO | WO 00/76438 A2 | 12/2000 |
| WO | WO 00/76439 A2 | 12/2000 |
| WO | WO 00/76442 A1 | 12/2000 |
| WO | WO 00/76443 A1 | 12/2000 |

* cited by examiner

*Primary Examiner*—Michele Kidwell
(74) *Attorney, Agent, or Firm*—Armstrong Teasdale, LLP

(57) ABSTRACT

A disposable absorbent article having an area which is visible when the article is worn. A color gradation in the area provides a coloration which varies in intensity over the area from a higher intensity of color to a lower intensity of color. A visible element, such as an indicator for indicating a change in condition of the article, is at a location where the coloration is of lower intensity or absent so as not to obscure visibility of the element.

20 Claims, 3 Drawing Sheets

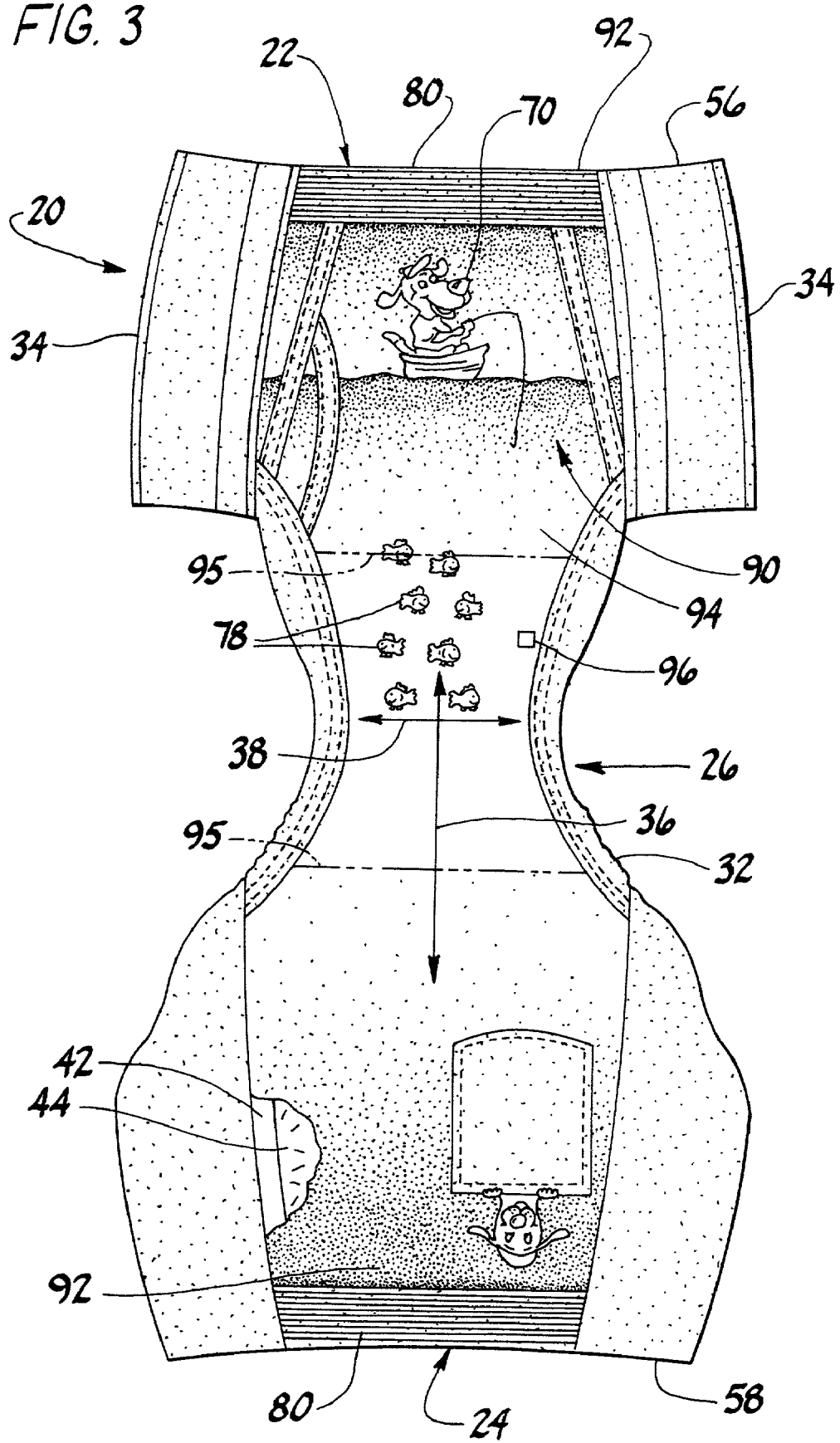

DISPOSABLE ABSORBENT ARTICLE HAVING A COLOR GRADATION FEATURE

BACKGROUND OF THE INVENTION

The present invention relates to absorbent articles, and more particularly to disposable absorbent articles having a gradation in color intensity visible when the article is worn.

The present invention is applicable to many different types of absorbent articles, including training pants, diapers, incontinence products, diaper pants, disposable underwear, medical garments, absorbent swim wear, and the like. It is especially (albeit not exclusively) suited to articles used in the toilet training process, a process which includes many training techniques and training aids that may be used by parents and caregivers (hereinafter simply referred to as caregivers). One aspect of the total toilet training process is the change from diapers to training pants to help the child understand that he or she should now use the toilet just like adults. Although the use of training pants and positive encouragement from the caregiver has been helpful in the toilet training process, there is still much room for improvement. Specifically, caregivers are still searching for easier and quicker ways to guide their children successfully through the toilet training process.

Many caregivers underestimate the difficulty of teaching the toilet training process to young children. If a child does not respond to an initial toilet training instruction or introduction, the caregiver can be at a loss for finding techniques, methods, or teaching tools to encourage the child to master the art of toilet training. Thus, while various teaching tools such as books, videotapes, charts with stickers, personalized toilets, and interactive toilet training kits are available, there remains a need for improved motivational mechanisms to facilitate the toilet training process.

One motivational mechanism is the use of training pants having an improved aesthetic appearance. Specifically, a child is encouraged to wear a garment which resembles underwear worn by older children or resembles outer garments worn by adults. These articles can have a moderately darker color or a color pattern on their front and back sides. Further, they may have a graphic, emblem, or pictorial image which is complemented by a background color, at least a portion of which is of moderate intensity. Unfortunately, most training pants have a solid light color or pastel background on their front and back sides, which can appear to be "babyish" to the child or otherwise fail to motivate the child to wear the garment.

Another motivational mechanism is the use of active graphics. As used herein, the term "active graphic" refers to an appearing graphic, a fading graphic, or a combination of fading and appearing graphics. The term "appearing graphic" is used herein to refer to a graphic that becomes visible or becomes significantly more visible when exposed to urine, or that becomes visible or becomes significantly more visible with the passage of time when exposed to the environment but not exposed to urine. Conversely, the term "fading graphic" is used herein to refer to a graphic that becomes invisible or becomes significantly less visible, or the color(s) "run" to obscure the graphic design, when exposed to urine, or that becomes invisible or becomes significantly less visible with the passage of time when exposed to the environment but not exposed to urine.

Active graphics should ideally be used on a lightly colored or white background. A darker background can obscure visibility of the graphics and/or obscure the mechanism of appearing or fading.

An active graphic can comprise a fading graphic which is formed from an ink that is soluble in aqueous solutions such as urine. The ink is positioned in the absorbent article so that it becomes wet and dissolves when the product is insulted with liquid. Once dissolved, or the colors(s) run, the ink washes away from the substrate on which it is printed and is obscured by the process of "running". As a result, the active graphic seems to disappear from view.

Suitable urine-soluble inks are available from a variety of commercial vendors, such as Sun Chemical Corp. of Philadelphia, Pa., USA under the trade designation AQUA DESTRUCT. Particular urine-soluble compositions are disclosed in U.S. Pat. No. 4,022,211 issued May 10, 1977 to Timmons et al., which is incorporated herein by reference. The ink color can be selected to provide a pleasing appearance and graphic impact, including fading rapidly upon contact with liquid. To facilitate rapid fading, the fading graphics can comprise line drawings having a line width of from about 1 to about 2 millimeters.

The active graphic can also comprise a fading or an appearing graphic which is formed from a composition such as an ink or adhesive that changes color when exposed to an aqueous solution such as urine. A color change composition can be adapted to blend in with a background or surrounding color, either before or after exposure to the aqueous solution. Suitable compositions of this color-change type are available from a variety of commercial vendors, such as a pH-change/color-change hot melt adhesive available from Findley Adhesives, Inc. of Wauwatosa, Wis., USA. Alternatively, the active graphic can comprise pH sensitive inks, fugitive inks, colored absorbent particles, hydratable salts, moisture sensitive films, enzymes, heat sensitive inks and dyes, or the like.

Fading graphics can simply disappear from view, relative to the exterior surface of the outer cover. The active graphic can also be configured to appear over time due to exposure to the environment. In particular, the active graphic can be responsive to time intervals, temperature levels, oxygen levels, or the like, and combinations thereof. Various visual indicators that appear over time in response to particular conditions are disclosed in U.S. Pat. No. 5,058,088 issued Oct. 15, 1991 to Haas et al.; U.S. Pat. No. 5,053,339 issued Oct. 1, 1991 to Patel; U.S. Pat. No. 5,045,283 issued Sep. 3, 1991 to Patel; U.S. Pat. No. 4,987,849 issued Jan. 29, 1991 to Sherman; U.S. Pat. No. 4,903,254 issued Feb. 20, 1990 to Haas; U.S. Pat. No. 4,812,053 issued Mar. 14, 1989 to Bhattacharjee; and U.S. Pat. No. 4,292,916 issued Oct. 6, 1981 to Bradley et al.; all of which are incorporated herein by reference. An active graphic that appears over time may be applied to the product when use is initiated, or formed as an integral component of the product.

In contrast to active graphics, the term "permanent graphic" is used herein to refer to a graphic that does not substantially change its degree of visibility when the absorbent article is insulted with urine and when the absorbent article is exposed to the environment, in actual or simulated use conditions.

The graphics of the absorbent article can be constructed to provide a story line involving a permanent character graphic and an active object graphic. The term "character graphic" is used herein to refer to a graphic containing an anthropomorphous image, and in particular an image having or suggesting human form or appearance which ascribes human motivations, characteristics or behavior to inanimate objects, animals, natural phenomena, cartoon characters, or the like. Suitable character graphics can include animals, people, inanimate objects, natural phenomena, cartoon characters, or the like that can or can not be provided with human features such as arms, legs, facial features or the like. For purposes of enhanced toilet training, it may be desirable for the character graphic to be familiar to the child, such as an identifiable cartoon character. The character graphics should at least be a type that the child can relate to, examples of which could include animals, toys, licensed characters, or the like. Character graphics can be made more personable and friendly to the child by including human-like features, human-like expressions, apparel, abilities, or the like. By way of illustration, an animal character graphic can be shown smiling, wearing clothing, playing sports, fishing, driving, playing with toys, or the like. In particular embodiments, the character graphic can desirably be created to project an appearance that could be described as friendly, positive, non-intimidating, silly, independent, inspirational, active, expressive, dauntless and/or persevering.

As referenced above, the permanent character graphic is desirably interactively interrelated with the active object graphic. The term "object graphic" is used herein to refer to a graphic representing an object or thing, which can include an inanimate object or a character. As used herein, "visible area" refers to structure or features externally visible while the absorbent article is worn.

For more detail regarding active graphics and their construction and operation, reference may be made to published PCT applications No. PCT/US00/16540 (Pub. No. WO 00/76438), entitled "Absorbent Articles Incorporating Color Change Graphics", No. PCT/US00/16542 (Pub. No. WO 00/76439), entitled "Absorbent Articles Having Wetness Indicating Graphics Incorporating a Training Zone", No. PCT/US00/16405 (Pub. No. WO 00/76442), entitled "Absorbent Articles Having Wetness Indicating Graphics Providing An Interactive Training Aid", and No. PCT/US00/16539 (Pub. No. WO 00/76443), entitled "Absorbent Articles Having Wetness Indicating Graphics and Employing Masking Techniques". These applications are assigned to Kimberly-Clark Worldwide, Inc., and are fully incorporated by reference herein for all purposes.

While the above improvements represent significant advances in the toilet training process, there is an ongoing need to increase the appeal of the toilet training process to children, and to improve the aesthetic appearance of disposable absorbent articles used in this process and other applications. It is advantageous for garments resemble underwear worn by older children. However, it is important that any modifications to the articles to meet these needs not compromise the use of the articles or any functional features of the articles (e.g., the wetness indicators).

SUMMARY OF THE INVENTION

In response to the needs identified above, an absorbent article has been developed having a graduated color feature which improves the aesthetic appearance of the article. For example, in the case of a training pant, the use of this color feature allows the pant to be made to have a more attractive appearance, thus making the toilet training process more appealing to children. The color feature can also be used to mask areas not intended to be seen, such as underlying anatomical features, bodily exudates, and/or interior structural components of the article itself. The color gradient does not detract in any way from the use of the article or the function of any indicator (e.g., wetness indicator) that may be employed with particular embodiments, since the indicator can be placed at a location where the coloration is of low intensity or completely absent. Further, the color feature of the present invention can be used with virtually any type of disposable absorbent article.

In general, a disposable absorbent article of the present invention has an area which is visible when the article is worn, and a color gradation in this area providing a coloration which varies in intensity over the area from a higher intensity of color to a lower intensity of color. A visible element is in the area at a location where the coloration is of lower intensity or absent so as not to obscure the visibility of the element.

In one particular embodiment, the article is a disposable absorbent pant having an outer cover with an interior surface and an opposite exterior surface, and an absorbent material disposed on the interior surface of the cover. The pant has front and back regions which define a waist region, and a crotch region extending between the front and back regions. A color gradation is on an area of the article which is visible when the article is worn. The color gradation provides a coloration which varies from a higher intensity of color in the vicinity of the waist region to a lower intensity of color toward the crotch region. A wetness indicator is in the crotch region at a location where the coloration is of lower intensity or absent so as not to obscure an indication of wetness by the wetness indicator.

The above-mentioned and other features and advantages of the present invention and the manner of attaining them will become more apparent, and the invention will be better understood by reference to the drawings and the following description of the drawings.

BRIEF DESCRIPTION OF THE DRAWINGS

FIG. 3 is a top plan, partially disassembled view of the training pant of FIGS. 1 and 2 in a stretched out and laid flat condition and with portions broken away for purposes of illustration.

Corresponding parts are indicated by corresponding reference numbers throughout the drawings.

DETAILED DESCRIPTION OF THE PREFERRED EMBODIMENT

The principles of the present invention can be incorporated into a variety of absorbent articles, and particularly disposable absorbent articles. The term "disposable" refers to articles which are designed to be discarded after a limited use rather than being laundered or otherwise restored for reuse. For ease of explanation, the description hereafter will be in terms of a child's training pant.

Figure 1:
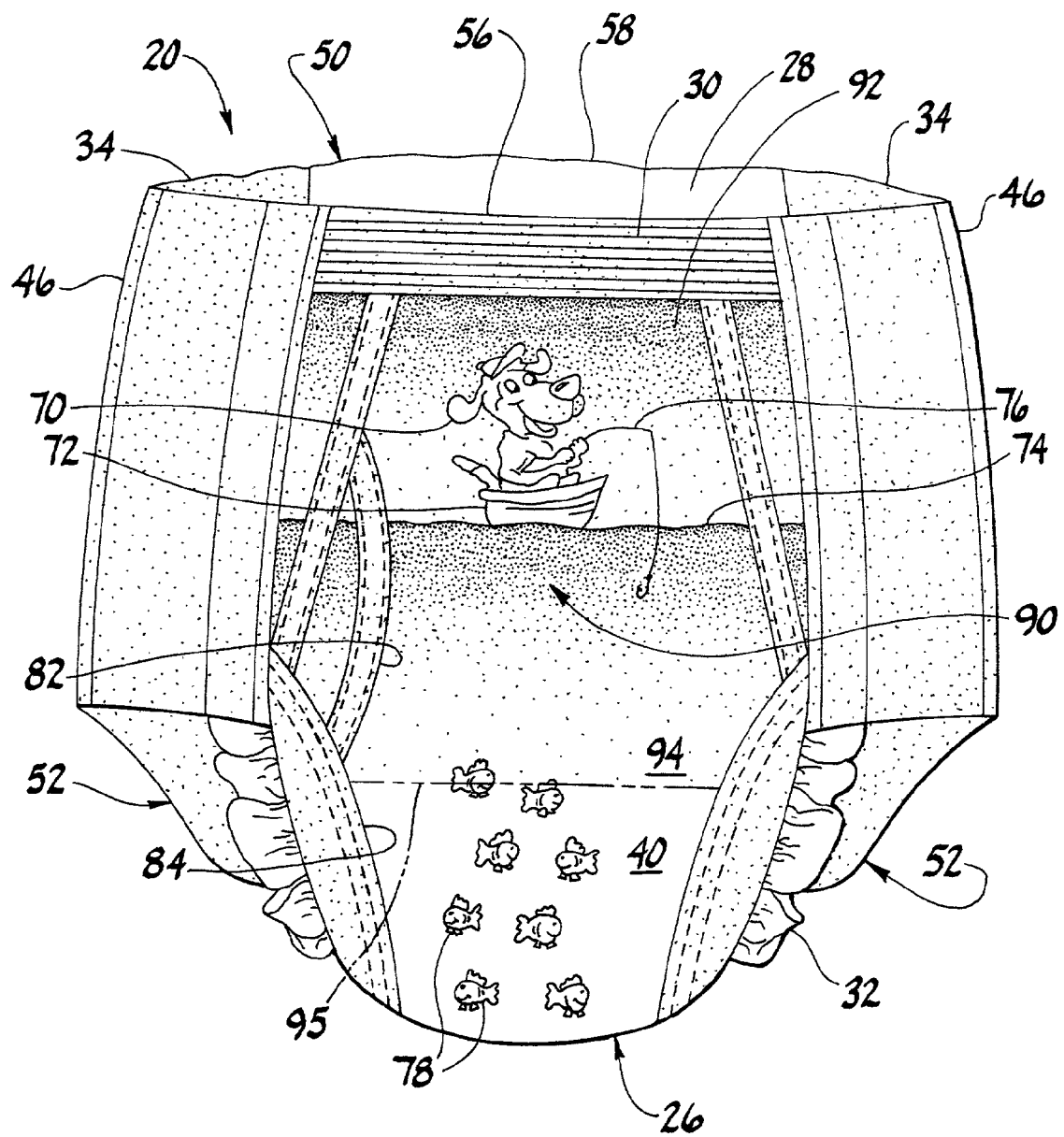
FIG. 1 is a front view of a training pant incorporating a color gradient feature of the present invention.
Figure 2:
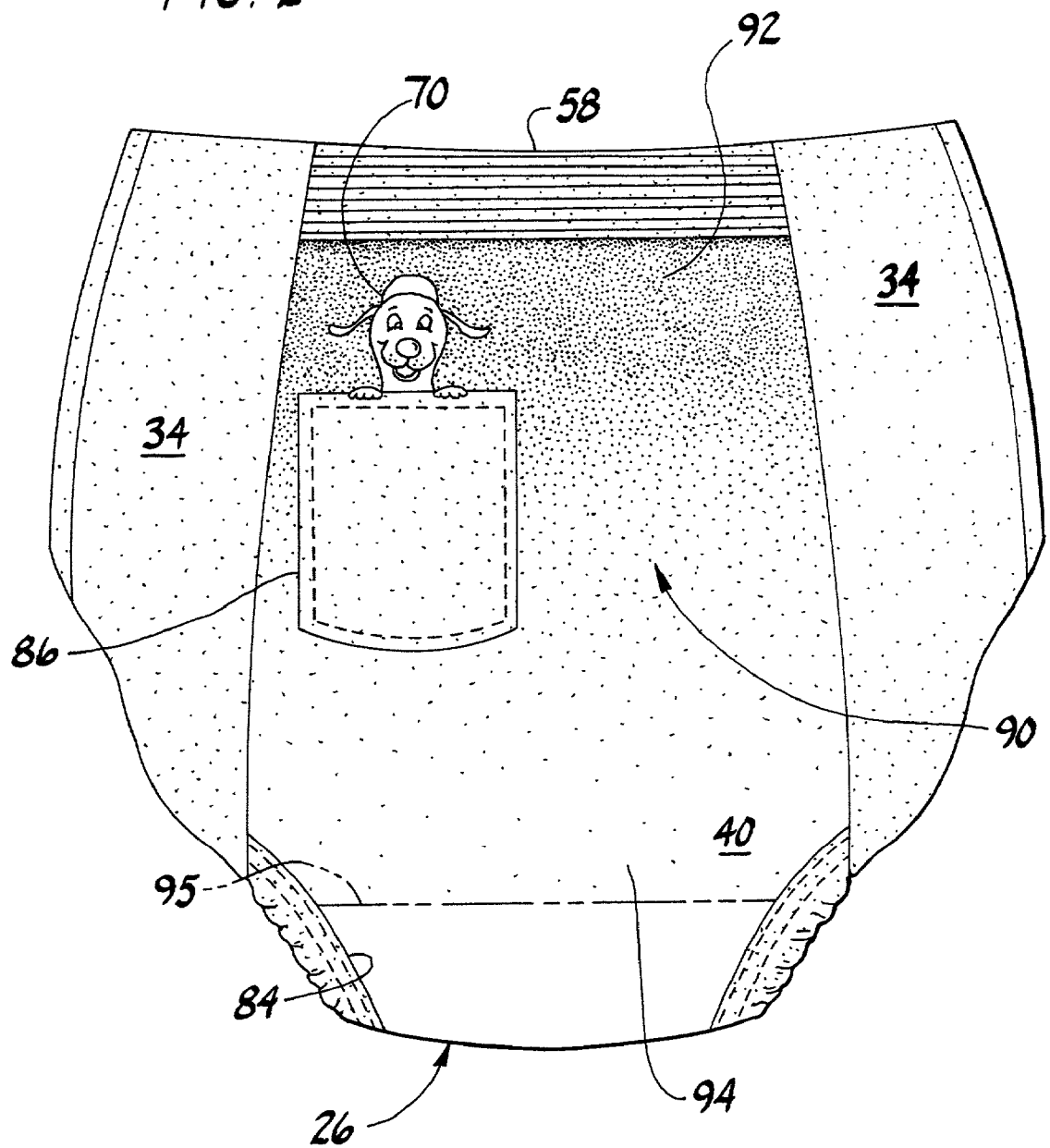
FIG. 2 is a rear view the training pant of FIG. 1.

Referring now to the drawings, a training pant 20 is illustrated in a fully assembled condition in FIGS. 1 and 2 and in a partially disassembled, stretched and laid flat condition in FIG. 3. The training pant 20 defines a first or front waist region 22, a second or back waist region 24, a crotch region 26 positioned between and interconnecting the front and back waist regions, an inner surface 28 (FIG. 1) which is configured to contact the wearer, and an outer surface 30 opposite the inner surface which is configured to contact the wearer's clothing. The illustrated training pant 20 comprises an absorbent chassis 32 and a plurality of transversely opposed side panels 34. The absorbent chassis 32 and side panels 34 can be integrally formed or comprise two or more separate elements, as shown.

The training pant 20 defines a longitudinal centerline 36 (FIG. 3), a transverse centerline 38 (FIG. 3), a first or front longitudinal end edge 56, and a second or back longitudinal end edge 58. The first waist region 22 abuts the first longitudinal end edge 56, and the second waist region 24 abuts the second longitudinal end edge 58. "Longitudinal" and "transverse" have their customary meaning. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

The illustrated absorbent chassis 32 comprises an outer cover 40 and a bodyside liner 42 (FIG. 3) which is connected to the outer cover in a superposed relation. The absorbent chassis 32 also comprises an absorbent assembly 44 (FIG. 3) which is located between the outer cover 40 and the bodyside liner 42, and can optionally include a pair of containment flaps (not shown).

With the training pant 20 in a fully assembled condition as illustrated in FIGS. 1 and 2, the front and back waist regions 22 and 24 are joined together by side seams 46 to define a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The side panels 34 comprise the portions of the training pant 20 which, when worn, are positioned on the side hip regions of the wearer. The longitudinal end edges 56 and 58 of the training pant 20 are configured to encircle the waist of the wearer when worn and provide the waist opening 50.

The absorbent chassis 32 is configured to contain and/or absorb any body exudates discharged from the wearer. For example, the absorbent chassis 32 desirably although not necessarily comprises the pair of containment flaps (not shown) which can be configured to provide a barrier to the transverse flow of body exudates. Suitable constructions and arrangements for the containment flaps are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 can include a front waist elastic member, a rear waist elastic member, and leg elastic members (not shown), as are known to those skilled in the art. Waist elastic members and leg elastic members can be operatively joined to the outer cover 40 and/or bodyside liner 42 of the training pant 20. Elastic members for the containment flaps, waist elastics and leg elastics can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic constrictive forces are imparted to the substrate. In one particular embodiment, for example, the leg elastic members comprise a plurality of dry-spun coalesced multifilament spandex elastomeric threads sold under the trade name LYCRA® and available from E. I. Du Pont de Nemours and Company, Wilmington, Del.

The outer cover 40 has an exterior surface corresponding to the outer surface 30 of the training pant and an opposite interior surface (not shown). The outer cover 40 preferably comprises a material which is substantially liquid impermeable. The outer cover 40 can be a single layer of liquid impermeable material, but preferably comprises a multi-layer laminate structure in which at least one of the layers is liquid impermeable.

For additional detail regarding the construction of the pant, including the cover 40, the bodyside liner 42 and the absorbent material 44, reference may be made to the aforesaid publications assigned to Kimberly-Clark Worldwide, Inc., incorporated herein by reference.

As shown in FIGS. 1-3, the training pant 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated training pant 20, which is designed for use by young boys, includes what may generally be referred to as an "indicator" for indicating a change in a condition of the pant, such as the wetness of the pant. In the particular embodiment shown, this indicator comprises interactive wetness indicating graphics. More specifically, the training pant includes a permanent character graphic 70 in the form of a dog having human-like expressions and wearing a shirt and a hat, permanent object graphics 72, 74 and 76 in the form of a boat, curved line segments denoting the surface of water, and a fishing pole, respectively, and a plurality of active object graphics 78 representing fish. The outer cover graphics also include a simulated elastic waistband 80, a simulated fly opening 82, simulated elastic leg bands 84, and a simulated back pocket 86, all of which can be permanent graphics.

The active object graphics 78 can be disposed on the interior surface of the outer cover 40 and are visible from the exterior surface of the outer cover. In particular embodiments, the active object graphics 78 can be disposed in liquid communication with the absorbent assembly 44, meaning that liquid such as urine is capable of moving between the active object graphic and the absorbent assembly under ordinary use conditions.

When the child wets the training pant 20, liquid is communicated to the active object graphics 78, whereupon the object graphics either dissolve, change color, appear, or the like. If fading graphics are used, for example, the graphics 78 disappear upon contact with urine. Where appearing graphics are employed, the situation would work in reverse and graphics would become visible upon liquid insult. Alternatively, the active object graphics 78 can comprise fading and/or appearing graphics that are triggered upon use by exposure to the environment.

In accordance with this invention, the training pant 20 has a coloration, and more specifically a color gradation, generally designated 90, on a visible area of the pant. The term "color gradation" as used herein refers to any visible change in coloration intensity resulting from a variation in color hue, brightness, lightness and/or a saturation of ink. The training pant 20 depicted in the Figures has a coloration which varies from a relatively higher intensity in the vicinity of the waist regions 22, 24 at the front and back of the pant, as indicated at 92 in FIGS. 1-3, to lower intensity toward the crotch region, as indicated at 94. A boundary area represented by line 95 indicates an approximate location separating a white colored area of the crotch from the beginning of shaded color. The transition can be gradual and the location of the boundary area 95 need not be visibly evident. Other locations of the boundary area do not depart from the scope of this invention. The side panels 34 of the pant are of a solid color in the embodiment shown in the drawings. Of course, the coloration of all areas of the pant, including the side panels, may vary, depending on the intended use of the pant. For example, in the case of a boy's pant, the overall color scheme may be blue, while a girl's pant may have more of a pink or yellow color scheme. The side panels may have a non-solid color or have a different intensity of color. The color gradation can also be used as an aspect of a permanent graphic, such as the surface of the water 74 (FIG. 1).

The use of a color gradation (or gradient) on the pant is beneficial for a number of reasons. For example, the higher intensity coloration can be used to create appearance features which increase the aesthetic appearance of the article. The coloration makes the pant appear more like colored underwear worn by older children or garments worn by adults by providing a portion of the front and back with moderately darker color or a color pattern. The higher intensity coloration can also be used to mask features not intended to be seen, such as underlying anatomical features, bodily exudates, or structural components of the pant. On the other hand, active graphics (or other visible elements contemplated by this invention), when employed, can be placed at locations where the coloration is of lower intensity, or where coloration is absent altogether, so that the graphics will not be obscured by the more intense coloration. The crotch region 26 of the pant in general, and the target spots for urine in particular, are areas where the active graphics may be placed, although other areas may also be suitable. If graphics that fade or appear when exposed to urine are used, it is especially important that they be placed in an area of low color intensity or no color whatsoever, to insure that the disappearance or appearance of such graphics after urination is not obscured. In general, however, it can be desirable to place a visual indicator in an area having low color intensity or no coloration, so that any signal of a change in condition is more readily apparent.

Although the invention is advantageous for use with an indicator showing a change in condition of the garment, such as an active graphic, it is understood that the invention includes any visible element which is not intended to be obscured by intense coloration being placed in a region where the coloration is less intense or absent. For example, a visible element such as an emblem, logo, or other feature which should remain visible at all times may be printed in such a region. Registration marks, such as the registration mark 96 shown in FIG. 3, may also be in that region for insuring that the active and/or permanent graphics are printed on the pant at the proper locations. The registration mark 96 may not be visible, but formed of an invisible ink or other material. It is understood that the color gradation of the present invention may be used alone, and not in conjunction with other visible elements or graphics.

The location, configuration, size and coloration of the color gradation feature of the present invention can vary widely. For example, the waist regions 22, 24 of the pant in the front and back may have a coloration of high intensity, with the coloration gradually fading toward the crotch region 26, leaving the crotch region substantially free of color, as shown in FIGS. 1-3. Alternatively, the color gradient may extend transversely with respect to the article, or at any angle relative to the longitudinal and transverse axes of the article, and can extend into or through the crotch region 26. The color gradation can be a smooth gradient providing a gradual fade, or a stepwise progression of color intensity. The coloration gradient may involve a single color, fading to white, or a combination of different colors, e.g., one color fading to another, such as green to yellow, or multiple blended colors fading gradually. Different color gradations can be used in different regions of the article, and the gradations can have different patterns (e.g., front-to-back, side-to-side, and/or telescoping where the gradations form a circular pattern, fading toward a circular area of white). The gradations can cover one continuous area or separate areas of similar or different sizes. The color gradation may extend a full dimension of the article (such as from one side seam to another, or from front waist to back waist through the crotch region), or it may encompass only a partial region of the article (e.g., only the front panel of the pant). Structural components of the pant (such as the waist or leg elastics) can be part of the area of color gradation. Alternatively, such components can be solid colored or uncolored to contrast with the other colored areas of the article. It will be understood that permanent graphics may be also used on the pant, suitably in the areas of greater color intensity.

The color gradation 90 of this invention may be provided by coloring any visible area of the pant with ink, preferably a permanent ink. For example, the area may be on the exterior surface of the outer cover 40, or the interior surface of the cover, or it may be on the absorbent assembly inside the outer cover or any other location so long as the coloration is visible when the pant is worn. The color is applied in suitable fashion, as by an ink printing process, to provide the necessary gradation. An example is a flexographic printing process, using lithographic plate technology, wherein a photopolymer plate containing the design is made from a film negative. The plate is put on a cylinder for printing to the surface of the pant. In one embodiment, the gradation may be provided by varying the dot (pixel) density of the ink over a given surface, the higher pixel densities providing coloration of higher intensity and the lower pixel densities providing coloration of lower intensity. A description of flexographic printing is found in U.S. Pat. No. 5,597,642, which is hereby incorporated by reference.

The outer cover 40 may be pre-printed with the color gradation applied on the outer surface of the cover, and the active graphic(s) applied on the opposite, inner cover, although other arrangements may also be suitable. The cover may then be combined with the absorbent assembly 44 and bodyside liner 42.

While the indicators discussed above for indicating a condition of the absorbent article are visual indicators which indicate wetness, it is contemplated that other conditions may be indicated, such as temperature, oxygen levels, UV light exposure, and the like. Moreover, the indicator may be a indicator which is hidden from view when the article is worn but which is capable of signaling a change in condition by non-visual means. For example, the indicator may be an area of the article which is designed to swell when it becomes wet and thereby apply pressure at a particular location to the body which can be felt by the wearer of the article. In this case, the color gradation feature of the present invention can be used to direct attention to the location of the indicator, if desired.

As various changes could be made in the above constructions without departing from the scope of the invention, it is intended that all matter contained in the above description or shown in the accompanying drawings shall be interpreted as illustrative and not in a limiting sense.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. "Disposed," "disposed on," "disposed with," "disposed at," "disposed near" and variations thereof are intended to mean that one element can be integral with another element, or that one element can be a separate structure bonded to or placed with or placed near another element.

What is claimed is:

1. A disposable absorbent article having an area which is visible when the article is worn, a color gradation in said area providing a coloration which varies in intensity over the area from a higher intensity of color to a lower intensity of color when the area is dry, and a visible element separate from said color gradation and disposed in said area at a location where the coloration of said color gradation is of lower intensity or absent such that the visible element remains visible and is not obscured by the color gradation.

2. A disposable absorbent article as set forth in claim 1 wherein said visible element is a graphic.

3. A disposable absorbent article as set forth in claim 1 wherein said visible element is a registration mark.

4. A disposable absorbent article as set forth in claim 1 wherein said visible element is a wetness indicator.

5. A disposable absorbent article as set forth in claim 4 further comprising an outer cover having an interior surface and an exterior surface, and an absorbent material disposed on said interior surface of the outer cover, said color gradation and said wetness indicator being disposed on said outer cover.

6. A disposable absorbent article as set forth in claim 5 wherein the article is a pant having a front region, a back region, and a crotch region, said wetness indicator being on a portion of the crotch region which is substantially free of color.

7. A disposable absorbent article as set forth in claim 6 wherein said coloration changes from higher intensity to lower intensity generally in the direction of said crotch region.

8. A disposable absorbent article as set forth in claim 6 wherein the pant further has side edges, said coloration changing from higher intensity to lower intensity generally in the direction of at least one of said side edges.

9. A disposable absorbent article as set forth in claim 7 or 8 wherein said color gradation involves only one color.

10. A disposable absorbent article as set forth in claim 7 or 8 wherein said color gradation involves a combination of different colors.

11. A disposable absorbent article as set forth in claim 4 wherein said wetness indicator comprises an active graphic.

12. A disposable absorbent article as set forth in claim 1 further comprising a graphic on said article, and a registration mark on said article for use in positioning said graphic on the article.

13. A disposable absorbent article as set forth in claim 12 wherein said article is a pant having a crotch region, and wherein said registration mark is located on said crotch region.

14. A disposable absorbent article as set forth in claim 1 wherein said color gradation is printed on the article in said area.

15. A disposable absorbent article as set forth in claim 14 wherein said color gradation is printed with a permanent ink.

16. A disposable absorbent pant having a front waist region, a back waist region and a crotch region extending between and interconnecting said front and back waist regions, said pant comprising an outer cover with an interior surface and an opposite exterior surface, an absorbent material disposed on the interior surface of the outer cover, a color gradation on an area of the pant which is visible when the pant is worn, said color gradation providing a coloration which varies from a higher intensity of color in the vicinity of the waist region to a lower intensity of color toward the crotch region when the pant is dry, and a wetness indicator separate from said color gradation and disposed in said crotch region at a location where the coloration of said color gradation is of lower intensity or absent such that any indication of wetness by the wetness indicator remains visible and is not obscured by the color gradation.

17. A disposable absorbent pant as set forth in claim 16 wherein said wetness indicator comprises an active graphic.

18. A disposable absorbent pant as set forth in claim 16 wherein said color gradation is printed in said area.

19. A disposable absorbent article having an area which is visible when the article is worn, a permanent graphic comprising a color gradation in said area providing a coloration which varies in intensity over the area from a higher intensity of color to a lower intensity of color, and a visible element separate from said permanent graphic and disposed in said area at a location where the coloration of said color gradation is of lower intensity or absent such that the visible element remains visible and is not obscured by the color gradation.

20. A disposable absorbent article comprising a color gradation that is visible when the article is worn, said color gradation comprising a coloration that varies in intensity from an area of higher intensity of color to a separate area of lower intensity of color, and a visible element separate from said color gradation and disposed at a location where the coloration of said color gradation is of lower intensity or absent such that the visible element remains visible and is not obscured by the color gradation.

\* \* \* \* \*